(12) United States Patent
Lassen et al.

(10) Patent No.: US 11,945,770 B1
(45) Date of Patent: Apr. 2, 2024

(54) CATALYTIC PROCESSES AND SYSTEMS FOR ALKYL SULFIDE PURIFICATION

(71) Applicant: Chevron Phillips Chemical Company LP, The Woodlands, TX (US)

(72) Inventors: Kenneth M. Lassen, Bartlesville, OK (US); Ugochukwu Nwagwu, Kingwood, TX (US); Jonathan Powell, Amarillo, TX (US); Daniel M. Hasenberg, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/179,188

(22) Filed: Mar. 6, 2023

(51) Int. Cl.
    *C07C 319/28*     (2006.01)
    *B01J 21/04*     (2006.01)
    *B01J 23/882*     (2006.01)
    *B01J 23/883*     (2006.01)
    *C07C 315/06*     (2006.01)

(52) U.S. Cl.
    CPC .............. *C07C 319/28* (2013.01); *B01J 21/04* (2013.01); *B01J 23/882* (2013.01); *B01J 23/883* (2013.01)

(58) Field of Classification Search
    CPC .................................................... C07C 319/28
    See application file for complete search history.

(56) References Cited

U.S. PATENT DOCUMENTS

| | | | | |
|---|---|---|---|---|
| 7,217,843 | B2 * | 5/2007 | Hasenberg | C07C 319/04 568/69 |
| 8,586,796 | B2 * | 11/2013 | Burkhardt | C07C 319/28 568/60 |
| 10,189,779 | B2 | 1/2019 | Lassen | |
| 10,774,040 | B1 | 9/2020 | Lassen et al. | |
| 10,927,074 | B2 | 2/2021 | Hasenberg et al. | |
| 11,174,225 | B2 | 11/2021 | Hasenberg et al. | |
| 2006/0140852 | A1 * | 6/2006 | Russell | C01B 3/38 423/652 |
| 2022/0106266 | A1 | 4/2022 | Kreider et al. | |

FOREIGN PATENT DOCUMENTS

EP      3992180      5/2022

* cited by examiner

*Primary Examiner* — Rosalynd A Keys
(74) *Attorney, Agent, or Firm* — Merchant & Gould P.C.

(57) ABSTRACT

The present disclosure provides for processes and systems for the purification of alkyl sulfide product streams including dimethyl sulfide (DMS). In some aspects, the disclosure provides for the removal of carbon disulfide ($CS_2$) from DMS via hydrolytic catalysis. In further embodiments, the disclosed catalytic processes are performed using mixed-metal catalyst systems such as cobalt-molybdenum (CoMo) and nickel-molybdenum (NiMo) catalyst systems.

32 Claims, No Drawings

CATALYTIC PROCESSES AND SYSTEMS FOR ALKYL SULFIDE PURIFICATION

FIELD

The present disclosure provides for processes and systems for purifying commercial alkyl sulfide product streams using mixed-metal catalytic compositions. In some embodiments, the disclosure relates to processes for purifying dimethyl sulfide (DMS) by the catalytic reduction or elimination of carbon disulfide ($CS_2$) from a DMS product stream. In further embodiments, the catalyst systems of the present disclosure comprise mixed-metal catalysts.

BACKGROUND

Alkyl sulfides comprise a commercially significant class of compounds, many of which are utilized in energy production, manufacturing, and food processing. The purity of these compounds is often optimized for enhancing the value and utility of alkyl sulfides, which includes the minimization or elimination of contaminants. Carbon disulfide ($CS_2$) is among the most common contaminants associated with alkyl sulfide chemical streams. Unfortunately, the conversion of $CS_2$ to more easily removable or recoverable contaminants or byproducts, such as hydrogen sulfide ($H_2S$), is often associated with the disadvantageous production of chemical species such as carbonyl sulfide (COS), which has been associated with deleterious activities such as acute animal toxicity and atmospheric ozone depletion.

It is therefore desirable to develop processes and methodologies that enhance alkyl sulfide purity and concentration while avoiding the challenges outlined above and known to those of skill in the relevant arts.

SUMMARY

The present disclosure provides for processes and systems for the purification of alkyl sulfides, including but not limited to the purification of alkyl sulfide product streams comprising dimethyl sulfide (DMS) using mixed-metal catalyst systems such as cobalt-molybdenum (CoMo) and nickel-molybdenum (NiMo) catalyst systems.

In some aspects, the present disclosure provides for a process for purifying an alkyl sulfide composition comprising 1) contacting the alkyl sulfide composition comprising carbon disulfide ($CS_2$) with water to form an aqueous alkyl sulfide product stream; 2) contacting the aqueous alkyl sulfide composition with a mixed-metal catalyst at a temperature in a range of from about 100° C. to about 300° C., a pressure in a range of from about 5 psig to about 300 psig, a molar ratio of water to $CS_2$ in a range of from about 10:1 to about 100:1, and a weight hourly space velocity (WHSV) in a range of from about 0.05 to about 5; and 3) hydrolyzing a least a portion of the $CS_2$ to form a purified alkyl sulfide product stream, which results in a purified alkyl sulfide product stream that, in some aspects, is characterized by no or essentially no detectable concentration of $CS_2$. In certain embodiments, the alkyl sulfide composition comprises an alkyl sulfide having the general formula $R^1$—S—$R^2$, where $R^1$ comprises a $C_1$ to $C_{18}$ substituted or unsubstituted, cycloalkyl group or linear or branched alkyl group; and $R^2$ comprises a $C_1$ to $C_{18}$ substituted or unsubstituted, cycloalkyl group or linear or branched alkyl group, including but not limited to compositions comprising dimethyl sulfide (DMS).

In some aspects, the process utilizes one or more mixed-metal catalysts, each of which comprises two or more Group 3-12 transition metals of the Periodic Table of Elements (*Chemical and Engineering News* 63(5), 27 (1985)), alternatively and commonly referred to as simply "transition metals." In accordance with the knowledge possessed by one of ordinary skill in the relevant art, a group of elements can be indicated using a common name assigned to the group; for example, alkali metals for Group 1 elements, alkaline earth metals for Group 2 elements, transition metals for Group 3-12 elements, pnictides for Group 15 elements, chalcogenides for Group 16 elements, and halogens or halides for Group 17 elements. In related embodiments, a mixed-metal catalyst may comprise two or more of cobalt (Co), molybdenum (Mo), and/or nickel (Ni), including but not limited to aspects wherein the mixed-metal catalyst comprises, for instant, a cobalt-molybdenum (CoMo) catalyst comprising from about 1 wt. % to about 5 wt. % cobalt, and from about 3 wt. % to about 20 wt. % molybdenum, or a nickel-molybdenum (NiMo) catalyst comprising: from about 1 wt. % to about 5 wt. % nickel, and from about 3 wt. % to about 20 wt. % molybdenum.

The mixed-metal catalysts for use in the disclosed processes and systems may further comprise or be characterized by a mixed-metal catalyst support, and may comprise a support or solid oxide, illustrative examples of which may include silica, alumina, silica-alumina, aluminum phosphate, zinc aluminate, thoria, magnesia, boria, titania, zirconia, a zeolite, combinations thereof, and the like. It is not intended that a mixed-metal catalyst support in accordance with the instant disclosure be limited to a particular material. For instance, as would be appreciated by the skilled artisan, an alumina-based catalyst support may comprise one or more particular alumina phases such as alpha ($\alpha$)-alumina, beta ($\beta$)-alumina, and/or gamma ($\gamma$)-alumina.

There are no particular limitations on the catalyst compositions used in the processes disclosed herein, as long as they are capable of promoting one or more reactions capable of purifying an alkyl sulfide composition and/or product stream, as described herein. In one aspect, the catalyst can comprise any suitable solid hydroprocessing catalyst. In another aspect, the catalyst can include a CoMo catalyst, a NiMo catalyst, and the like, as well as any combination thereof. In particular aspects, the mixed-metal catalyst may comprise a CoMo catalyst and alumina catalyst support, such as a CoMo catalyst/$\gamma$-alumina catalyst support system, including but not limited to commercially available catalysts and catalyst supports such as the HR-306 and HR-316 catalysts available from Axens SA (Rueil-Malmaison, FR), and the KF-752, KF-756, and KF-757 catalysts available from Akzo Nobel N.V. (Amsterdam, NL).

In some aspects, the catalyst may comprise supported CoMo and an alkali or alkaline earth metal hydroxide as described, for instance, in U.S. Pat. No. 4,277,623, incorporated herein by reference in its entirety. For example, although the respective amounts of Co and Mo are not limited thereto, the catalyst may comprise about 1 to about 5 wt. % cobalt (including salts thereof, such as cobalt oxides), and about 3 to about 20 wt. % molybdenum (including molybdenum salts thereof, such as molybdenum oxide) that are further supported on alumina. The relative amounts of the supported CoMo component are not particularly limited.

As noted herein, the disclosed processes and systems are beneficially capable of reducing the concentration of deleterious species such as carbon disulfide ($CS_2$) in an alkyl sulfide product stream, such as a dimethyl sulfide (DMS)

product stream, for beneficially enhancing the purity and concentration of the desired product(s). For example, in certain embodiments the disclosed process is capable of producing an alkyl sulfide product stream that is characterized by a carbon disulfide ($CS_2$) concentration of less than about 1000 parts per million (ppm), including less than about 500 ppm, about 100 ppm, about 10 ppm, about 5 ppm, about 2 ppm, and about 1 ppm.

The processes and systems disclosed herein may advantageously be modified with respect to one or more parameters such as temperature, pressure, weight hourly space velocity (WHSV), etc. For instance, step (ii) of the process may be performed may be performed under conditions such as a temperature in a range of from about 125° C. to about 225° C.; a pressure in a range of about 10 psig to about 100 psig; and a WHSV in a range of from about 0.20 to about 1.5; in additional aspects, step (ii) may be performed at a temperature in a range of from about 130° C. to about 150° C.; a pressure in a range of about 25 psig to about 75 psig; and a WHSV in a range of from about 0.25 to about 0.75.

In accordance with aspects of the instant disclosure, the processes and systems described herein may be performed in any commercially available vessel(s), reactor(s), etc., known to the skilled artisan, including arrangements or designs directed to the use of one or more vessels selected from a flow reactor, a continuous reactor, a packed tube, and a stirred tank reactor, as well as combinations of the foregoing, including but not limited to, for instance, processes and systems where at least two vessels arranged either in series or in parallel.

Additional aspects of the disclosed processes and systems relate to the introduction of the feedstream to the catalyst bed as well as the reaction/retention time(s) for converting undesirable compounds such as $CS_2$ to more readily removable species such as $CO_2$ and $H_2S$. For example, in embodiments the contacting of an aqueous alkyl sulfide composition with a mixed-metal catalyst of the disclosed process may occur over a time period in a range of about 1 minute to about 48 hours, including but not limited to a time period in a range of about 5 minutes to about 8 hours.

DETAILED DESCRIPTION

The present disclosure provides for processes and systems for use in the purification of commercial product streams comprising alkyl sulfides. The purification processes and systems may utilize catalytic compositions comprising one or more transition metals, included mixed-metal systems, and are characterized by the surprisingly efficient conversion of deleterious chemical species such as carbon disulfide ($CS_2$) into compounds that are more easily removed from the product stream such as carbon dioxide ($CO_2$) and hydrogen sulfide ($H_2S$).

As used herein, the terms "alkyl sulfide," "organic sulfide," "organosulfide," and "organosulfur" each refer to a compound comprising at least one alkyl group and at least one sulfide group. In non-limiting aspects, an alkyl sulfide reactant in accordance with the present disclosure, including an alkyl sulfide reactant stream or product stream, may comprise or consist of dimethyl sulfide (DMS), which may alternatively be referred to as methylthiomethane or methyl sulfide. Additional alkyl sulfide chemical species for use in accordance with certain aspects of the present disclosure include diethyl sulfide, dipropyl sulfide, dibutyl sulfide, dihexyl sulfide, and dioctyl sulfide.

In accordance with certain aspects and features of the disclosed processes and systems, the terms "catalyst" and "catalyst compound" refer to a compound capable of initiating catalysis and/or of promoting one or more chemical reactions without being chemically or physically consumed during the reaction(s). The catalyst or catalyst compound may interchangeably be described as one or more of a catalyst precursor, a pre-catalyst compound, or a transition metal compound comprising or consisting of one or more transition metals and/or coordinated transition metal compounds. In accordance with certain features, the catalyst/catalyst compound is not poisoned or otherwise inactivated while catalyzing or promoting a reaction as described herein.

In accordance with some aspects of the technology, a catalyst compound may be utilized or employed in the absence of additional chemical and/or physical compounds or components for performing catalysis or, alternatively, it may be used in combination with one or more activators. When the catalyst compound is combined with an activator to initiate catalysis, the catalyst compound is often referred to as a pre-catalyst or catalyst precursor. A "catalyst system," as described herein, may encompass a combination of at least one catalyst compound, one or more catalyst activators, one or more optional co-activators, and/or one or more optional support materials.

As used in the instant disclosure, the term "comprising" may be used to describe the presence or utilization of various compositions, components, steps, etc. In addition, the processes and systems of the instant disclosure may "consist essentially of" or "consist of" various compositions, components, steps, etc., unless specifically exemplified or described otherwise.

As used herein, the term "about" refers to amounts, sizes, formulations, parameters, additional quantities/characteristics, etc., capable of approximation including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. As would be appreciated by those of skill in the relevant art, "about" further encompasses amounts that vary due to, for example, differing equilibrium conditions for a composition resulting from a particular feedstream or initial mixture. Whether or not modified by the term "about," the claims include equivalents to the quantities. In related aspects, "about" may encompass values that are within 10% of a reported numerical value, including within 5% of a reported numerical value.

In accordance with the relevant portions of the present disclosure, the terms "contacting" and "combining" may be utilized to describe processes and systems wherein the compositions, substrates, materials, components, etc., are combined in any non-limiting order, manner, length of time, etc., unless otherwise specified. For example, the materials or components can be blended, mixed, slurried, dissolved, reacted, treated, compounded, and/or impregnated by any process, method, and/or technique known to those of skill in the relevant art.

As used herein, "a," "an," and "the" are not to be interpreted as unduly limiting, and are expressly intended to include plural alternatives, for instance, at least one, unless otherwise specified. For example, terms and phrases of the present disclosure such as "a higher boiling point product" and "an alkyl sulfide" are meant to encompass one, or mixtures or combinations of more than one, higher boiling point product and alkyl sulfide, respectively, unless otherwise specified.

The processes and systems described herein are advantageously useful for enhancing the value of an alkyl sulfide product streams by, in certain aspects, hydrolyzing impurities such as carbon sulfide ($CS_2$) for beneficially enhancing the concentration and purity of the product stream. For instance, one of the most commercially significant alkyl sulfides is dimethyl sulfide (DMS), the product streams of which may contain well over 1000 ppm by weight $CS_2$, including 2000-4000 ppm by weight or greater of $CS_2$. Although the foregoing concentrations can be reduced via filtration, adsorption, and related techniques for achieving concentrations, e.g., of about 20 ppm or less, DMS product streams characterized by a $CS_2$ concentration of less than about 5 ppm, including about 1 ppm, are often required for catalytic, comestible, and additional commercial applications.

The alkyl sulfide product streams disclosed in and contemplated by the present disclosure for use in the methods and systems disclosed herein are not limited to any product concentration or concentration range, nor is the corresponding impurity concentration, e.g., $CS_2$ concentration, similarly limited. For example, aspects of the disclosure provide for alkyl sulfide product streams comprises at least about 80 wt. %, at least about 85 wt. %, or at least about 90 wt. %, and more often, the alkyl sulfide product stream comprises at least about 95 wt. %, at least about 98 wt. %, at least about 99 wt. %, or at least about 99.9 wt. %, of the alkyl sulfide product compound. In certain embodiments, the alkyl sulfide product stream may comprise or consist of recycled alkyl sulfide product for optimizing production conditions, reducing costs, etc. For instance, processes and methodologies associated with the production of dimethyl sulfide (DMS), in accordance with aspects of the present disclosure, may include the incorporation of recycled DMS in at least a portion of a DMS product stream.

Embodiments of the disclosed processes and systems are beneficially capable of reducing the associated cost of alkyl sulfide production, such as dimethyl sulfide (DMS) production. While in no way limiting the disclosure to any particular theory or chemical pathway(s), it is believed that DMS (($CH_3$)$_2$S) can be synthesized via the reaction of hydrogen sulfide ($H_2S$) with methanol ($CH_3OH$) as follows:

$$H_2S + 2CH_3OH \rightarrow (CH_3)_2S + 2H_2O.$$

In related aspects, the production of DMS in accordance with one or more of the disclosed processes and/or systems may be associated with beneficial increases in the $H_2S$:$CH_3OH$ ratio associated with the foregoing equation.

In certain aspects, the temperature, which may be alternatively referred to as a weighted average temperature (WAT) or a weighted average bed temperature (WABT), at which an alkyl sulfide stream is treated for the removal of $CS_2$ via hydrolysis may be manipulated, i.e., increased or decreased, as necessary for optimizing the catalytic conversion of $CS_2$ to $CO_2$. For example, in particular embodiments an alkyl sulfide stream comprises or consists essentially of dimethyl sulfide (DMS), e.g., at a concentration of greater than about 95% by weight (95 wt. %), including greater than about 97 wt. %, greater than about 99.0 wt. %, and about 99.5 wt. % or greater. While in no way limiting the present technology to any particular chemical theory or mechanism(s), it is believed that the purification or enrichment of DMS via $CS_2$ hydrolysis may proceed, regardless of whether the $CS_2$ is present in gaseous (g) or liquid (l) form, as follows:

$$CS_{2(g)} + 2H_2O_{(g)} \rightarrow CO_{2(g)} + 2H_2S_{(g)} \quad \Delta H_{rxn} = -29909 \text{ BTU/lb·mol} \quad (1)$$

$$CS_{2(l)} + 2H_2O_{(l)} \rightarrow CO_{2(g)} + 2H_2S_{(g)} \quad \Delta H_{rxn} = +20611 \text{ BTU/lb·mol} \quad (2)$$

Although the processes and methodologies of the instant disclosure are not limited, for instance, to the physical state of the alkyl sulfide stream, including any contaminants present in the stream, in some aspects the disclosed processes and methodologies may be optimized when the alkyl sulfide stream and contaminants, such as $CS_2$, are present in the gaseous phase. Aspects of this potential optimization are reflected, for instance, in the advantageous reaction enthalpy ($\Delta H_{rxn}$) associated with equation (1) above.

In related embodiments, the pressure at which an alkyl sulfide stream is treated for the removal of $CS_2$ via hydrolysis may be increased or decreased as necessary for optimizing the catalytic conversion of $CS_2$ to $CO_2$. For instance, in non-limiting aspects the hydrolysis processes and reactions described herein may be performed at one or more pressures in a range of about 5 pounds per square inch gauge (psig) to about 300 psig, including a range of about 10 psig to about 100 psig, a range of about 25 psig to about 75 psig, and a range of about 40 psig to about 60 psig, including a pressure value of about 50 psig. In certain embodiments, the rate and/or conversion of $CS_2$ to $CO_2$ may be advantageously enhanced by performing the hydrolysis reaction at a pressure value of about 50 psig, or lower.

Aspects of the instant disclosure encompass the beneficial use of lower temperature conditions for significantly reducing or eliminating pernicious $CS_2$ components from an alkyl sulfide product stream such as a dimethyl sulfide (DMS) product stream. For example, in embodiments a process temperature capable of reducing or eliminating $CS_2$ from DMS, including processes capable of producing a product stream of about 100% DMS (i.e., a product stream with no detectable $CS_2$) is in a range of about 50° C. to about 400° C., including about 75° C. to about 300° C., about 100° C. to about 200° C., about 125° C. to about 175° C., and about 130° C. to about 150° C., including a temperature of about 140° C.

In addition, the liquid hourly space velocity (LHSV) associated with one or more of the processes disclosed herein may be manipulated to optimize $CS_2$ removal from an alkyl sulfide product stream, including but not limited to a DMS product stream. For instance, in certain aspects a purification process disclosed herein may be characterized by a LHSV value of about 1 or less, including a LHSV value in a range of about 0.1 to about 0.9, about 0.2 to about 0.8, about 0.3 to about 0.7, and about 0.4 to about 0.6, including a LHSV value of about 0.5, or about 0.6.

Aspects of one or more of the disclosed processes may further include the utilization of a particular combination of processing conditions that synergistically optimize the hydrolysis (and subsequent removal) of $CS_2$ from an alkyl sulfide product stream such as DMS. For example, in a non-limiting embodiment a process for purifying an alkyl sulfide product stream in accordance with the instant disclosure may feature, inter alia, a WHSV of in a range of about 0.5 to about 0.6, a weight average temperature (WAT) of about 140° C., and pressure in a range of about 50 psig to about 100 psig.

In embodiments, the disclosed processes may be performed using any type of equipment or equipment component capable of reducing the $CS_2$ concentration in an alkyl sulfide product stream, including but not limited to a $CS_2$ hydrolysis reactor. In non-limiting aspects, this equipment and/or equipment component may comprise a dedicated reactor such as a hydrolysis reactor capable of hydrolyzing alkyl sulfide product stream contaminants such as $CS_2$. The placement of such a $CS_2$ hydrolysis reactor is not limited to any particular placement or location in a chemical processing plant or processing subunit. For example, in particular embodiments a $CS_2$ hydrolysis reactor (and any necessary, supporting equipment or components) may be positioned within a methyl methionine (MeSH) chemical production facility between a hydrogen sulfide ($H_2S$) stripping apparatus, alternatively referred to as a "$H_2S$ stripper," and a wash column, e.g., a methanol water wash column. Such an arrangement could, for example, beneficially utilize the methanol water wash column as a repository for any excessive water that is introduced into the $CS_2$ hydrolysis reactor would be removed in the water wash column.

In additional embodiments, a static mixer, such as an in-line static mixer capable of mixing water with an alkyl sulfide product stream comprising contaminants such as $CS_2$, may be positioned or added immediately upstream of a $CS_2$ hydrolysis reactor for beneficially enhancing the purification of the associated product stream. In related embodiments, the molar concentration and/or molar ratio of water ($H_2O$) is significantly greater relative to the concentration and/or ratio of $CS_2$, including $H_2O:CS_2$ ratios of at least 10:1, at least 25:1, at least 50:1, and at least 100:1.

Aspects of the disclosure related to the type and/or phase of water for use in the present disclosure should not be construed as limiting. For instance, the water utilized in the processes or methodologies disclosed herein may comprise untreated water, deionized (DI) water, reclaimed water, and/or condensate, any of which may be present in the form of liquid or steam.

Examples

In accordance with aspects of the present disclosure, two separate catalyst systems capable of hydrolyzing $CS_2$ were investigated. The samples referenced in Tables I and II below were analyzed using a Hewlett-Packard (HP) 6890 Plus gas chromatograph equipped with a thermal conductivity detector (TCD; HP Inc., Spring, TX, USA).

The first catalyst system comprised a cobalt-molybdenum/alumina catalyst system such as those described in U.S. Pat. No. 7,217,843 (assigned to Chevron Phillips Chemical Company LP), which is incorporated herein by reference in its entirety. When a DMS solution comprising $CS_2$ was introduced to the foregoing catalyst system under operating conditions of a weight-hourly space velocity (WHSV) of about 0.5, a temperature of about 140° C., and a pressure of about 50 psig, a 100% conversion of 1 weight percentage (1 wt. %) $CS_2$ fraction of a DMS solution was observed (see Table I below). As further shown in Table I, a similar conversion percentage was observed for a separate DMS solution comprising 0.75 wt. % $CS_2$.

The second catalyst system, comprising a nickel-molybdenum catalyst such as those described in U.S. Pat. No. 7,645,906 (assigned to Chevron Phillips Chemical Company LP), which is incorporated herein by reference in its entirety, was operated at a weight-hourly space velocity (WHSV) of about 0.5, was similarly operated under conditions necessary to produce 100% $CS_2$ conversion for a 0.75 wt. % $CS_2$ fraction of a DMS solution (see Table II). While similar WHSV and pressure conditions of about 0.5 and about 50 psig, respectively, were sufficient, a significant temperature elevation (in excess of 250° C. in some trials (Table II) was required to produce the desired $CS_2$ conversion.

While certain aspects of the technology have been shown and described, modifications thereof may be made by one skilled in the art without departing from the spirit and teachings of the technology. The aspects described herein are exemplary only, and are not intended to be limiting. Many variations and modifications of the technology disclosed herein are possible and are within the scope of the technology. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

The use of the term "optionally," with respect to any element of a claim or feature, is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. The claims are a further description of and an addition to the aspects of the present disclosure. The disclosures of all patents, patent applications, and publications cited herein are hereby incorporated by reference, to the extent that they provide exemplary, procedural, or other details supplementary to those set forth herein.

TABLE I

| Catalyst grams | Press psig | DMS/$CS_2$ gms/hr | DI-$H_2O$ gms/hr | WHSV | LHSV | $H_2O$/$CS_2$ mole ratio | Top T ° C. | Mid T ° C. | Btm T ° C. | WAT ° C. | $CO_2$ Wt % | $H_2S$ Wt % | $H_2O$ Wt % | MeSH Wt % | DMS Wt % | $CS_2$ Wt % | $CS_2$ Conversion Wt % |
|---|---|---|---|---|---|---|---|---|---|---|---|---|---|---|---|---|---|
| | | 0.75% $CS_2$ | | | | | | | | | | | | | | | |
| 89.09 | 49 | 50 | 3 | 0.56 | 0.51 | 34 | 95 | 197 | 172 | 154.7 | 0.14 | 0.34 | 1.16 | 0.83 | 76.80 | 0.00 | 100.00 |
| 89.09 | 49 | 49 | 3 | 0.55 | 0.50 | 34 | 91 | 192 | 172 | 151.7 | 0.14 | 0.51 | 0.80 | 0.87 | 77.21 | 0.00 | 100.00 |
| 89.09 | 50 | 50 | 4 | 0.56 | 0.51 | 45 | 98 | 186 | 171.0 | 151.7 | 0.00 | 0.47 | 1.94 | 0.75 | 75.70 | 0.00 | 100.00 |
| 89.09 | 50 | 49 | 4 | 0.55 | 0.50 | 46 | 104 | 188 | 170.0 | 154.0 | 0.16 | 0.50 | 1.75 | 0.66 | 76.05 | 0.00 | 100.00 |
| 89.09 | 49 | 50 | 4 | 0.56 | 0.51 | 45 | 114 | 225 | 197.0 | 178.7 | 0.16 | 0.58 | 2.19 | 0.83 | 75.16 | 0.00 | 100.00 |
| 89.09 | 50 | 50 | 3 | 0.56 | 0.51 | 34 | 119 | 228 | 197.0 | 181.3 | 0.13 | 0.56 | 3.34 | 1.58 | 72.75 | 0.00 | 100.00 |
| 89.09 | 50 | 50 | 3 | 0.56 | 0.14 | 34 | 121 | 226 | 197.0 | 181.3 | 0.15 | 0.46 | 4.43 | 1.70 | 71.16 | 0.00 | 100.00 |
| | | 1.0% $CS_2$ | | | | | | | | | | | | | | | |
| 89.09 | 50 | 50 | 4 | 0.56 | 0.51 | 34 | 29 | 26 | 28.0 | 27.7 | 0.09 | 0.06 | 1.54 | 0.53 | 76.90 | 0.21 | 78.93 |
| 89.09 | 50 | 49 | 3 | 0.55 | 0.50 | 26 | 29 | 25 | 28.0 | 27.3 | 0.00 | 0.00 | 1.21 | 0.11 | 77.55 | 0.61 | 38.14 |

TABLE I-continued

| Catalyst grams | Press psig | DMS/CS$_2$ gms/hr | DI-H$_2$O gms/hr | WHSV | LHSV | H$_2$O/CS$_2$ mole ratio | Top T °C. | Mid T °C. | Btm T °C. | WAT °C. | CO$_2$ Mol % | H$_2$S Mol % | H$_2$O Mol % | MeSH Mol % | DMS Mol % | CS$_2$ Mol % | CS$_2$ Conversion Mol % |
|---|---|---|---|---|---|---|---|---|---|---|---|---|---|---|---|---|---|
| 89.09 | 50 | 49 | 3 | 0.55 | 0.50 | 26 | 29 | 25 | 28.0 | 27.3 | 0.00 | 0.00 | 1.04 | 0.00 | 77.77 | 0.74 | 24.30 |
| 89.09 | 61 | 50 | 3 | 0.56 | 0.51 | 25 | 82 | 93 | 2.0 | 59.0 | 0.00 | 0.00 | 1.93 | 0.06 | 76.44 | 0.71 | 27.52 |
| 89.09 | 51 | 49 | 3 | 0.55 | 0.50 | 26 | 87 | 88 | 100.0 | 91.7 | 0.00 | 0.00 | 1.86 | 0.06 | 76.56 | 0.69 | 29.89 |
| 89.09 | 49 | 49 | 3 | 0.55 | 0.50 | 26 | 86 | 90 | 101.0 | 92.3 | 0.00 | 0.00 | 2.15 | 0.00 | 76.28 | 0.68 | 30.57 |
| 89.09 | 50 | 50 | 4 | 0.56 | 0.51 | 34 | 88 | 88 | 100.0 | 92.0 | 0.00 | 0.00 | 1.92 | 0.00 | 76.54 | 0.68 | 39.55 |
| 89.09 | 50 | 50 | 3 | 0.56 | 0.51 | 25 | 89 | 91 | 100.0 | 93.3 | 0.00 | 0.00 | 2.54 | 0.00 | 75.65 | 0.67 | 31.97 |
| 89.09 | 50 | 49 | 4 | 0.55 | 0.50 | 34 | 87 | 92 | 99.0 | 92.7 | 0.00 | 0.00 | 1.91 | 0.00 | 76.55 | 0.68 | 30.44 |
| 89.09 | 50 | 50 | 3 | 0.56 | 0.51 | 25 | 90 | 119 | 123.0 | 110.7 | 0.09 | 0.18 | 1.81 | 0.08 | 76.50 | 0.56 | 43.09 |
| 89.09 | 50 | 49 | 3 | 0.55 | 0.50 | 26 | 90 | 118 | 123.0 | 110.3 | 0.00 | 0.20 | 1.74 | 0.07 | 76.74 | 0.50 | 49.26 |
| 89.09 | 50 | 50 | 3 | 0.56 | 0.51 | 25 | 89 | 118 | 123.0 | 110.0 | 0.00 | 0.19 | 1.76 | 0.00 | 76.80 | 0.48 | 50.83 |
| 89.09 | 50 | 50 | 3 | 0.56 | 0.51 | 25 | 90 | 120 | 123.0 | 111.0 | 0.00 | 0.18 | 1.83 | 0.00 | 76.72 | 0.48 | 51.12 |
| 89.09 | 49 | 49 | 3 | 0.55 | 0.50 | 26 | 88 | 119 | 123.0 | 110.0 | 0.00 | 0.16 | 2.90 | 0.00 | 75.08 | 0.48 | 50.73 |
| 89.09 | 52 | 50 | 3 | 0.56 | 0.51 | 25 | 92 | 136 | 180.0 | 122.7 | 0.00 | 0.26 | 1.39 | 0.08 | 76.37 | 0.43 | 56.01 |
| 89.09 | 50 | 50 | 3 | 0.56 | 0.51 | 25 | 94 | 142 | 141.0 | 125.7 | 0.09 | 0.35 | 1.87 | 0.11 | 76.58 | 0.20 | 79.39 |
| 89.09 | 50 | 49 | 4 | 0.55 | 0.50 | 34 | 94 | 166 | 137.0 | 132.3 | 0.10 | 0.37 | 1.38 | 0.12 | 77.38 | 0.06 | 93.42 |
| 89.09 | 51 | 50 | 3 | 0.56 | 0.51 | 25 | 104 | 168 | 138.0 | 136.7 | 0.11 | 0.41 | 3.45 | 0.15 | 74.36 | 0.00 | 100.00 |
| 89.09 | 50 | 49 | 3 | 0.55 | 0.50 | 26 | 95 | 168 | 145.0 | 136.0 | 0.11 | 0.42 | 1.56 | 0.19 | 77.08 | 0.00 | 100.00 |
| 89.09 | 219 | 50 | 3 | 0.56 | 0.51 | 25 | 123 | 140 | 143 | 137.0 | 0.00 | 0.00 | 27.80 | 0.00 | 39.52 | 0.00 | 100.00 |
| 89.09 | 218 | 49 | 3 | 0.55 | 0.50 | 26 | 124 | 140 | 150 | 138.0 | 0.16 | 0.35 | 3.72 | 0.19 | 76.64 | 0.00 | 100.00 |
| 89.09 | 221 | 50 | 3 | 0.56 | 0.51 | 25 | 128 | 144 | 143 | 140.3 | 0.16 | 0.37 | 1.45 | 0.17 | 77.06 | 0.00 | 100.00 |
| 89.09 | 223 | 49 | 3 | 0.55 | 0.50 | 26 | 130 | 146 | 150 | 142.0 | 0.15 | 0.41 | 1.72 | 0.16 | 76.50 | 0.00 | 100.00 |
| 89.09 | 220 | 49 | 3 | 0.55 | 0.50 | 26 | 130 | 148 | 150 | 142.7 | 0.15 | 0.45 | 0.06 | 0.16 | 74.85 | 0.00 | 100.00 |
| 89.09 | 277 | 50 | 3 | 0.56 | 0.51 | 25 | 130 | 150 | 152 | 144.0 | 0.12 | 0.41 | 3.28 | 0.15 | 74.60 | 0.00 | 100.00 |
| 89.09 | 371 | 49 | 4 | 0.55 | 0.50 | 34 | 126 | 158 | 148 | 144.0 | 0.16 | 0.38 | 2.44 | 0.22 | 75.76 | 0.00 | 100.00 |
| 89.09 | 375 | 49 | 4 | 0.55 | 0.50 | 34 | 127 | 158 | 147 | 144.0 | 0.17 | 0.38 | 1.94 | 0.28 | 78.73 | 0.00 | 100.00 |
| 89.09 | 378 | 50 | 3 | 0.56 | 0.51 | 25 | 127 | 158 | 147 | 144.0 | 0.17 | 0.37 | 1.22 | 0.25 | 77.42 | 0.08 | 92.12 |
| 89.09 | 397 | 50 | 3 | 0.56 | 0.51 | 25 | 126 | 157 | 147 | 143.3 | 0.18 | 0.40 | 2.12 | 0.24 | 76.08 | 0.09 | 90.59 |
| 89.09 | 450 | 50 | 4 | 0.56 | 0.51 | 34 | 120 | 154 | 145 | 139.7 | 0.16 | 0.37 | 2.83 | 0.31 | 75.55 | 0.00 | 100.00 |
| 89.09 | 450 | 49 | 4 | 0.55 | 0.50 | 34 | 120 | 152 | 146 | 139.3 | 0.15 | 0.33 | 4.97 | 0.24 | 71.99 | 0.11 | 88.56 |
| 89.09 | 450 | 51 | 3 | 0.57 | 0.52 | 25 | 122 | 151 | 146 | 139.7 | 0.16 | 0.36 | 2.28 | 0.22 | 75.85 | 0.16 | 83.68 |
| 89.09 | 448 | 49 | 3 | 0.55 | 0.50 | 26 | 116 | 151 | 145 | 137.3 | 0.15 | 0.37 | 2.82 | 0.21 | 75.07 | 0.17 | 83.17 |
| 89.09 | 436 | 50 | 3 | 0.56 | 0.51 | 25 | 125 | 155 | 151 | 143.7 | 0.15 | 0.38 | 2.24 | 0.21 | 75.89 | 0.17 | 82.50 |
| 89.09 | 442 | 50 | 4 | 0.56 | 0.51 | 34 | 128 | 158 | 154 | 148.7 | 0.16 | 0.40 | 2.18 | 0.21 | 75.94 | 0.19 | 81.00 |
| 89.09 | 450 | 50 | 3 | 0.56 | 0.51 | 25 | 130 | 162 | 157 | 149.7 | 0.14 | 0.35 | 12.61 | 0.22 | 60.92 | 0.09 | 91.23 |
| 89.09 | 450 | 49 | 4 | 0.55 | 0.50 | 34 | 132 | 163 | 160 | 151.7 | 0.14 | 0.42 | 3.38 | 0.32 | 74.35 | 0.07 | 92.83 |
| 89.09 | 450 | 50 | 3 | 0.56 | 0.51 | 25 | 132 | 165 | 160 | 152.3 | 0.17 | 0.44 | 2.46 | 0.37 | 75.46 | 0.05 | 94.46 |
| 89.09 | 450 | 50 | 4 | 0.56 | 0.51 | 34 | 134 | 165 | 160 | 153.0 | 0.08 | 0.18 | 32.55 | 0.14 | 32.19 | 0.06 | 93.48 |
| 89.09 | 446 | 50 | 4 | 0.56 | 0.51 | 34 | 136 | 167 | 162 | 155.0 | 0.16 | 0.43 | 3.41 | 0.44 | 74.08 | 0.00 | 100.00 |
| 89.09 | 450 | 50 | 3 | 0.56 | 0.51 | 25 | 139 | 169 | 162 | 156.7 | 0.16 | 0.39 | 7.28 | 0.43 | 68.50 | 0.00 | 100.00 |
| 89.09 | 450 | 50 | 4 | 0.56 | 0.51 | 34 | 139 | 173 | 163 | 158.3 | 0.00 | 0.00 | 11.95 | 0.00 | 62.62 | 0.00 | 100.00 |

| Catalyst grams | Press psig | DMS/CS$_2$ gms/hr | DI-H$_2$O gms/hr | WHSV | LHSV | H$_2$O/CS$_2$ mole ratio | Top T °C. | Mid T °C. | Btm T °C. | WAT °C. | CO$_2$ Mol % | H$_2$S Mol % | H$_2$O Mol % | MeSH Mol % | DMS Mol % | CS$_2$ Mol % | CS$_2$ Conversion Mol % |
|---|---|---|---|---|---|---|---|---|---|---|---|---|---|---|---|---|---|
| | | 0.75% CS$_2$ | | | | | | | | | | | | | | | |
| 89.09 | 49 | 50 | 3 | 0.56 | 0.51 | 34 | 95 | 197 | 172 | 154.7 | 0.24 | 0.76 | 4.89 | 1.31 | 93.79 | 0.000 | 100.00 |
| 89.09 | 49 | 49 | 3 | 0.55 | 0.50 | 34 | 91 | 192 | 172 | 151.7 | 0.24 | 1.14 | 3.38 | 1.38 | 95.24 | 0.000 | 100.00 |
| 89.09 | 50 | 50 | 4 | 0.56 | 0.51 | 45 | 98 | 186 | 171.0 | 151.7 | 0.00 | 1.03 | 8.03 | 1.16 | 90.81 | 0.000 | 100.00 |
| 89.09 | 50 | 49 | 4 | 0.55 | 0.50 | 46 | 104 | 188 | 170.0 | 154.0 | 0.26 | 1.10 | 7.26 | 1.03 | 91.71 | 0.000 | 100.00 |
| 89.09 | 49 | 50 | 4 | 0.56 | 0.51 | 45 | 114 | 225 | 197.0 | 178.7 | 0.28 | 1.26 | 9.00 | 1.28 | 89.71 | 0.000 | 100.00 |
| 89.09 | 50 | 50 | 3 | 0.56 | 0.51 | 34 | 119 | 228 | 197.0 | 181.3 | 0.22 | 1.18 | 13.33 | 2.37 | 84.30 | 0.000 | 100.00 |
| 89.09 | 50 | 50 | 3 | 0.56 | 0.14 | 34 | 121 | 226 | 197.0 | 181.3 | 0.26 | 0.95 | 17.23 | 2.47 | 80.30 | 0.000 | 100.00 |
| | | 1.0% CS$_2$ | | | | | | | | | | | | | | | |
| 89.09 | 50 | 50 | 4 | 0.56 | 0.51 | 34 | 29 | 26 | 28.0 | 27.7 | 0.16 | 0.14 | 6.38 | 0.82 | 92.59 | 0.203 | 75.31 |
| 89.09 | 50 | 49 | 3 | 0.55 | 0.50 | 26 | 29 | 25 | 28.0 | 27.3 | 0.00 | 0.00 | 5.04 | 0.17 | 94.19 | 0.601 | 26.89 |
| 89.09 | 50 | 49 | 3 | 0.55 | 0.50 | 26 | 29 | 25 | 28.0 | 27.3 | 0.00 | 0.00 | 4.36 | 0.00 | 94.90 | 0.739 | 10.10 |
| 89.09 | 61 | 50 | 3 | 0.56 | 0.51 | 25 | 82 | 93 | 2.0 | 59.0 | 0.00 | 0.00 | 7.93 | 0.09 | 91.28 | 0.693 | 15.77 |
| 89.09 | 51 | 49 | 3 | 0.55 | 0.50 | 26 | 87 | 88 | 100.0 | 91.7 | 0.00 | 0.00 | 7.67 | 0.09 | 91.57 | 0.671 | 18.40 |
| 89.09 | 49 | 49 | 3 | 0.55 | 0.50 | 26 | 86 | 90 | 101.0 | 92.3 | 0.00 | 0.00 | 8.61 | 0.00 | 90.73 | 0.661 | 19.84 |
| 89.09 | 50 | 50 | 4 | 0.56 | 0.51 | 34 | 88 | 88 | 100.0 | 92.0 | 0.00 | 0.00 | 7.90 | 0.00 | 91.44 | 6.664 | 19.27 |
| 89.09 | 50 | 50 | 3 | 0.56 | 0.51 | 25 | 89 | 91 | 100.0 | 93.3 | 0.00 | 0.00 | 10.31 | 0.00 | 89.05 | 0.641 | 22.06 |
| 89.09 | 50 | 49 | 4 | 0.55 | 0.50 | 34 | 87 | 92 | 99.0 | 92.7 | 0.00 | 0.00 | 7.87 | 0.00 | 91.47 | 9.665 | 19.12 |
| 89.09 | 50 | 50 | 3 | 0.56 | 0.51 | 25 | 90 | 119 | 123.0 | 110.7 | 0.15 | 0.40 | 7.48 | 0.13 | 91.85 | 0.547 | 33.52 |
| 89.09 | 50 | 49 | 3 | 0.55 | 0.50 | 26 | 90 | 118 | 123.0 | 110.3 | 0.00 | 0.43 | 7.20 | 0.11 | 92.20 | 0.488 | 40.67 |
| 89.09 | 50 | 50 | 3 | 0.56 | 0.51 | 25 | 89 | 118 | 123.0 | 110.0 | 0.00 | 0.42 | 7.26 | 0.00 | 92.27 | 0.473 | 42.52 |
| 89.09 | 50 | 50 | 3 | 0.56 | 0.51 | 25 | 90 | 120 | 123.0 | 111.0 | 0.00 | 0.39 | 7.54 | 0.00 | 92.00 | 0.469 | 42.96 |
| 89.09 | 49 | 49 | 3 | 0.55 | 0.50 | 26 | 88 | 119 | 123.0 | 110.0 | 0.00 | 0.33 | 11.90 | 0.00 | 87.64 | 0.460 | 44.03 |
| 89.09 | 52 | 50 | 3 | 0.56 | 0.51 | 25 | 92 | 136 | 140.0 | 122.7 | 0.00 | 0.57 | 8.18 | 0.12 | 91.28 | 0.421 | 48.84 |
| 89.09 | 50 | 50 | 3 | 0.56 | 0.51 | 25 | 94 | 142 | 141.0 | 125.7 | 0.15 | 0.76 | 7.73 | 0.18 | 91.90 | 0.198 | 75.93 |
| 89.09 | 50 | 49 | 4 | 0.55 | 0.50 | 34 | 94 | 166 | 137.0 | 132.3 | 0.17 | 0.81 | 5.80 | 0.19 | 93.95 | 0.064 | 92.22 |
| 89.09 | 51 | 50 | 3 | 0.56 | 0.51 | 25 | 104 | 168 | 138.0 | 136.7 | 0.17 | 0.87 | 13.75 | 0.23 | 86.02 | 0.000 | 100.00 |
| 89.09 | 50 | 49 | 3 | 0.55 | 0.50 | 26 | 95 | 168 | 145.0 | 136.0 | 0.18 | 0.93 | 6.49 | 0.29 | 93.22 | 0.000 | 100.00 |
| 89.09 | 219 | 50 | 3 | 0.56 | 0.51 | 25 | 123 | 140 | 148 | 137.0 | 0.00 | 0.00 | 70.79 | 0.00 | 29.21 | 0.000 | 100.00 |
| 89.09 | 218 | 49 | 3 | 0.55 | 0.50 | 26 | 124 | 140 | 150 | 138.0 | 0.28 | 0.82 | 7.14 | 0.30 | 92.56 | 0.000 | 100.00 |

TABLE I-continued

| | | | | | | | | | | | | | | | | | | | |
|---|---|---|---|---|---|---|---|---|---|---|---|---|---|---|---|---|---|---|---|
| 89.09 | 221 | 50 | 3 | 0.56 | 0.51 | 25 | 128 | 144 | 149 | 140.3 | 0.27 | 0.96 | 6.20 | 0.27 | 93.54 | 0.000 | 100.00 | | |
| 89.09 | 223 | 49 | 3 | 0.55 | 0.50 | 26 | 130 | 146 | 150 | 142.0 | 0.26 | 0.98 | 7.14 | 0.25 | 92.61 | 0.000 | 100.00 | | |
| 89.09 | 220 | 49 | 3 | 0.55 | 0.50 | 26 | 130 | 148 | 150 | 142.7 | 0.25 | 0.97 | 12.30 | 0.24 | 87.46 | 0.000 | 100.00 | | |
| 89.09 | 277 | 50 | 3 | 0.56 | 0.51 | 25 | 130 | 150 | 152 | 144.0 | 0.20 | 0.87 | 13.13 | 0.23 | 86.64 | 0.000 | 100.00 | | |
| 89.09 | 371 | 49 | 4 | 0.55 | 0.50 | 34 | 126 | 158 | 148 | 144.0 | 0.26 | 0.83 | 9.94 | 0.33 | 89.73 | 0.000 | 100.00 | | |
| 89.09 | 375 | 49 | 4 | 0.55 | 0.50 | 34 | 127 | 158 | 147 | 144.0 | 0.28 | 0.83 | 7.97 | 0.44 | 91.59 | 0.000 | 100.00 | | |
| 89.09 | 378 | 50 | 3 | 0.56 | 0.51 | 25 | 127 | 158 | 147 | 144.0 | 0.29 | 0.83 | 5.13 | 0.40 | 94.40 | 0.077 | 90.65 | | |
| 89.09 | 397 | 50 | 3 | 0.56 | 0.51 | 25 | 126 | 157 | 147 | 143.3 | 0.30 | 0.87 | 8.69 | 0.37 | 90.85 | 0.090 | 89.06 | | |
| 89.09 | 450 | 50 | 4 | 0.56 | 0.51 | 34 | 120 | 154 | 145 | 139.7 | 0.26 | 0.80 | 10.29 | 0.47 | 89.24 | 0.000 | 100.00 | | |
| 89.09 | 450 | 49 | 4 | 0.55 | 0.50 | 34 | 120 | 152 | 146 | 139.3 | 0.24 | 0.68 | 19.12 | 0.35 | 80.43 | 0.102 | 87.56 | | |
| 89.09 | 450 | 51 | 3 | 0.57 | 0.52 | 25 | 122 | 151 | 146 | 139.7 | 0.26 | 0.77 | 9.34 | 0.34 | 90.17 | 0.155 | 81.12 | | |
| 89.09 | 448 | 49 | 3 | 0.55 | 0.50 | 26 | 116 | 151 | 145 | 137.3 | 0.24 | 0.79 | 11.40 | 0.32 | 88.13 | 8.158 | 80.78 | | |
| 89.09 | 436 | 50 | 3 | 0.56 | 0.51 | 25 | 125 | 155 | 151 | 143.7 | 0.26 | 0.83 | 9.17 | 0.32 | 90.34 | 0.167 | 79.73 | | |
| 89.09 | 442 | 50 | 4 | 0.56 | 0.51 | 34 | 128 | 158 | 154 | 146.7 | 0.26 | 0.87 | 8.95 | 0.33 | 90.54 | 0.187 | 77.95 | | |
| 89.09 | 450 | 50 | 3 | 0.56 | 0.51 | 25 | 130 | 162 | 157 | 149.7 | 0.20 | 0.61 | 41.46 | 0.27 | 58.20 | 0.067 | 91.84 | | |
| 89.09 | 450 | 49 | 4 | 0.55 | 0.50 | 34 | 132 | 163 | 160 | 151.7 | 0.23 | 0.88 | 13.12 | 0.48 | 86.34 | 0.067 | 91.90 | | |
| 89.09 | 450 | 50 | 3 | 0.56 | 0.51 | 25 | 132 | 165 | 160 | 152.3 | 0.28 | 0.95 | 10.02 | 0.57 | 89.36 | 0.052 | 93.62 | | |
| 89.09 | 450 | 50 | 4 | 0.56 | 0.51 | 34 | 134 | 165 | 160 | 153.0 | 0.08 | 0.23 | 77.54 | 0.16 | 22.27 | 0.036 | 95.61 | | |
| 89.09 | 446 | 50 | 4 | 0.56 | 0.51 | 34 | 136 | 167 | 162 | 155.0 | 0.26 | 0.91 | 13.59 | 0.66 | 85.78 | 0.000 | 100.00 | | |
| 89.09 | 450 | 50 | 3 | 0.56 | 0.51 | 25 | 139 | 169 | 162 | 156.7 | 0.23 | 0.76 | 26.63 | 0.59 | 72.78 | 0.000 | 100.00 | | |
| 89.09 | 450 | 50 | 4 | 0.56 | 0.51 | 34 | 139 | 173 | 163 | 158.3 | 0.00 | 0.00 | 39.65 | 0.00 | 60.35 | 0.000 | 100.00 | | |

TABLE II

| Catalyst grams | $DMS/CS_2$ mole ratio 0.75% $CS_2$ | Press psig | $DMS/CS_2$ gms/hr .75% $CS_2$ | DI-$H_2O$ gms/hr | $H_2O/CS_2$ mole ratio | WHSV | Top T °C. | Mid T °C. | Btm T °C. | WAT °C. | $CO_2$ Wt % | $H_2S$ Wt % |
|---|---|---|---|---|---|---|---|---|---|---|---|---|
| | | | | 0 | | | | | | | 0.00 | 0.00 |
| 86.05 | 0.13 | 54 | 74 | 3 | 23 | 0.86 | 90 | 90 | 95.0 | 92.0 | 0.00 | 0.04 |
| 86.05 | 0.19 | 45 | 50 | 3 | 34 | 0.58 | 88 | 96 | 107.8 | 97.0 | 0.00 | 0.04 |
| 86.05 | 0.19 | 45 | 49 | 3 | 34 | 0.57 | 88 | 96 | 100.0 | 94.7 | 0.00 | 0.05 |
| 86.05 | 0.19 | 45 | 49 | 3 | 34 | 0.57 | 93 | 121 | 130.0 | 114.7 | 0.00 | 0.05 |
| 86.05 | 0.26 | 45 | 49 | 4 | 46 | 0.57 | 93 | 130 | 130.0 | 117.7 | 0.00 | 0.08 |
| 86.05 | 0.25 | 45 | 50 | 4 | 45 | 0.58 | 95 | 131 | 129 | 118.3 | 0.00 | 0.07 |
| 86.05 | 0.26 | 45 | 49 | 4 | 46 | 0.57 | 103 | 132 | 125.0 | 120.0 | 0.00 | 0.08 |
| 86.05 | 0.19 | 45 | 49 | 3 | 34 | 0.57 | 100 | 134 | 123.0 | 119.0 | 0.00 | 0.08 |
| 86.05 | 0.19 | 45 | 50 | 3 | 34 | 0.58 | 102 | 134 | 122.0 | 119.3 | 0.00 | 0.07 |
| 86.05 | 0.3 | 45 | 50 | 4 | 45 | 0.58 | 105 | 151 | 149.0 | 135.0 | 0.00 | 0.03 |
| 86.05 | 0.2 | 45 | 49 | 3 | 34 | 0.57 | 101 | 149 | 149.0 | 133.0 | 0.00 | 0.05 |
| 86.05 | 0.2 | 45 | 49 | 3 | 34 | 0.57 | 103 | 148 | 149.0 | 133.3 | 0.00 | 0.06 |
| 86.05 | 0.2 | 50 | 50 | 3 | 34 | 0.58 | 111 | 181 | 184.0 | 158.7 | 0.01 | 0.11 |
| 86.05 | 0.3 | 50 | 50 | 4 | 45 | 0.58 | 117 | 184 | 171.0 | 157.3 | 0.03 | 0.26 |
| 86.05 | 0.2 | 50 | 49 | 3 | 34 | 0.57 | 123 | 182 | 170.0 | 158.3 | 0.05 | 0.30 |
| 86.05 | 0.19 | 50 | 50 | 3 | 34 | 0.58 | 145 | 205 | 200 | 183.3 | 0.06 | 0.31 |
| 86.05 | 0.19 | 50 | 49 | 3 | 34 | 0.57 | 148 | 218 | 200 | 188.7 | 0.09 | 0.63 |
| 86.05 | 0.25 | 50 | 50 | 4 | 45 | 0.58 | 145 | 214 | 199 | 186.0 | 0.10 | 0.65 |
| 86.05 | 0.25 | 50 | 50 | 4 | 45 | 0.58 | 174 | 235 | 229 | 212.7 | 0.10 | 0.61 |
| 86.05 | 0.25 | 50 | 50 | 4 | 45 | 0.58 | 175 | 239 | 224 | 212.7 | 0.12 | 0.81 |
| 86.05 | 0.19 | 63 | 49 | 3 | 34 | 0.57 | 191 | 248 | 238 | 225.7 | 0.15 | 0.48 |
| 86.05 | 0.19 | 55 | 50 | 3 | 34 | 0.58 | 189 | 250 | 238 | 225.7 | 0.12 | 0.54 |
| 86.05 | 0.26 | 55 | 49 | 4 | 46 | 0.57 | 195 | 250 | 239 | 228.0 | 0.14 | 0.55 |
| 86.05 | 0.19 | 59 | 50 | 3 | 34 | 0.58 | 198 | 249 | 338 | 228.3 | 0.13 | 0.52 |
| 86.05 | 0.19 | 68 | 50 | 3 | 34 | 0.58 | 197 | 248 | 238 | 227.7 | 0.14 | 0.50 |
| 86.05 | 0.19 | 62 | 49 | 3 | 34 | 0.57 | 195 | 251 | 239 | 228.3 | 0.14 | 0.49 |
| 86.05 | 0.25 | 71 | 50 | 4 | 45 | 0.58 | 213 | 262 | 252 | 242.3 | 0.13 | 0.49 |
| 86.05 | 0.25 | 68 | 50 | 4 | 45 | 0.58 | 208 | 268 | 254 | 243.3 | 0.12 | 0.46 |
| 86.05 | 0.26 | 63 | 49 | 4 | 46 | 0.57 | 216 | 264 | 253 | 244.3 | 0.12 | 0.41 |

| $H_2O$ Wt % | MeSH Wt % | DMS Wt % | $CS_2$ Wt % | $CO_2$ Mol % | $H_2S$ Mol % | $H_2O$ Mol % | MeSH Mol % | DMS Mol % | $CS_2$ Mol % | $CS_2$ Cnvrsn Wt % | $CS_2$ Cnvrsn Mol % |
|---|---|---|---|---|---|---|---|---|---|---|---|
| 0.07 | 0.00 | 79.12 | 0.75 | 0.00 | 0.00 | 0.31 | 0.00 | 98.93 | 0.76 | | |
| 0.51 | 0.00 | 73.74 | 0.70 | 0.00 | 0.10 | 2.32 | 0.00 | 96.83 | 0.75 | 6.80 | 2.11 |
| 0.74 | 0.00 | 75.92 | 1.13 | 0.00 | 0.09 | 3.22 | 0.00 | 95.53 | 1.16 | −50.55 | −51.51 |
| 0.99 | 0.00 | 76.19 | 0.71 | 0.00 | 0.11 | 4.25 | 0.00 | 94.92 | 0.72 | 5.04 | 5.27 |
| 1.44 | 0.00 | 75.60 | 0.84 | 0.00 | 0.10 | 6.09 | 0.00 | 92.96 | 0.84 | −12.17 | −10.32 |
| 2.29 | 0.02 | 75.22 | 0.77 | 0.00 | 0.16 | 9.39 | 0.02 | 89.67 | 0.75 | −2.85 | 1.94 |
| 5.98 | 0.02 | 70.09 | 0.69 | 0.00 | 0.14 | 22.53 | 0.03 | 76.68 | 0.62 | 7.46 | 19.02 |
| 2.33 | 0.02 | 75.42 | 0.74 | 0.00 | 0.18 | 9.51 | 0.03 | 89.57 | 0.72 | 1.32 | 6.26 |
| 1.86 | 0.02 | 76.18 | 0.75 | 0.00 | 0.18 | 7.67 | 0.03 | 91.39 | 0.74 | −0.88 | 3.21 |
| 1.45 | 0.01 | 76.81 | 0.76 | 0.00 | 0.15 | 6.05 | 0.02 | 93.02 | 0.75 | −1.43 | 1.75 |
| 1.62 | 0.00 | 74.84 | 0.73 | 0.00 | 0.07 | 6.87 | 0.00 | 92.33 | 0.74 | 2.30 | 3.61 |
| 1.78 | 0.00 | 76.11 | 0.74 | 0.00 | 0.11 | 7.40 | 0.00 | 91.76 | 0.73 | 0.88 | 4.42 |
| 1.83 | 0.00 | 76.33 | 0.75 | 0.00 | 0.14 | 7.55 | 0.00 | 91.58 | 0.73 | −0.22 | 3.83 |
| 1.60 | 0.02 | 76.63 | 0.75 | 0.02 | 0.24 | 6.65 | 0.03 | 92.32 | 0.74 | −0.66 | 3.01 |

TABLE II-continued

| | | | | | | | | | | | |
|---|---|---|---|---|---|---|---|---|---|---|---|
| 2.44 | 0.02 | 75.29 | 0.69 | 0.05 | 0.56 | 9.92 | 0.03 | 88.77 | 0.67 | 7.24 | 12.53 |
| 2.68 | 0.04 | 74.76 | 0.66 | 0.09 | 0.64 | 10.84 | 0.06 | 87.74 | 0.63 | 12.06 | 17.46 |
| 2.07 | 0.02 | 75.73 | 0.62 | 0.10 | 0.68 | 8.49 | 0.03 | 90.10 | 0.61 | 16.56 | 20.80 |
| 2.65 | 0.06 | 74.56 | 0.51 | 0.15 | 1.34 | 10.68 | 0.08 | 87.26 | 0.49 | 31.36 | 35.75 |
| 2.40 | 0.05 | 75.02 | 0.45 | 0.16 | 1.40 | 9.72 | 0.08 | 88.21 | 0.43 | 39.91 | 43.49 |
| 3.36 | 0.07 | 73.69 | 0.44 | 0.17 | 1.27 | 13.38 | 8.10 | 84.76 | 0.41 | 41.67 | 46.34 |
| 5.48 | 0.15 | 70.39 | 0.33 | 0.19 | 1.61 | 20.64 | 0.22 | 77.06 | 0.29 | 56.47 | 61.88 |
| 7.69 | 0.68 | 66.85 | 0.82 | 0.22 | 0.92 | 27.75 | 0.92 | 70.09 | 0.10 | 99.87 | 86.30 |
| 6.84 | 0.86 | 68.08 | 0.07 | 0.18 | 1.05 | 25.05 | 1.18 | 72.48 | 0.06 | 99.92 | 91.69 |
| 3.68 | 0.94 | 72.74 | 0.05 | 0.22 | 1.15 | 14.40 | 1.38 | 82.80 | 0.04 | 99.95 | 94.11 |
| 3.22 | 1.03 | 73.38 | 0.04 | 0.21 | 1.09 | 12.74 | 1.53 | 84.38 | 0.03 | 99.96 | 95.56 |
| 3.19 | 1.11 | 73.47 | 0.02 | 0.22 | 1.05 | 12.61 | 1.64 | 84.45 | 0.02 | 99.97 | 96.98 |
| 2.03 | 1.13 | 75.19 | 0.04 | 0.23 | 1.05 | 8.25 | 1.72 | 88.71 | 0.03 | 99.96 | 95.55 |
| 1.39 | 1.39 | 75.88 | 0.03 | 0.23 | 1.07 | 5.71 | 2.15 | 90.82 | 0.03 | 99.97 | 96.64 |
| 2.66 | 1.83 | 73.56 | 0.02 | 0.19 | 0.92 | 10.62 | 2.75 | 85.45 | 0.02 | 99.98 | 97.56 |
| 3.16 | 1.94 | 72.86 | 0.03 | 0.19 | 0.86 | 12.47 | 2.87 | 83.58 | 0.03 | 99.97 | 96.58 |

What is claimed is:

1. A process for purifying an alkyl sulfide composition, the process comprising:
   (i) contacting the alkyl sulfide composition comprising carbon disulfide ($CS_2$) and at least 80 wt. % of an alkyl sulfide with water to form an aqueous alkyl sulfide composition;
   (ii) contacting the aqueous alkyl sulfide composition with a mixed-metal catalyst at
       a temperature in a range of from about 100° C. to about 300° C.,
       a pressure in a range of from about 5 psig to about 300 psig,
       a molar ratio of water to $CS_2$ in a range of from about 10:1 to about 100:1, and
       a weight hourly space velocity (WHSV) in a range of from about 0.05 to about 5; and
   (iii) hydrolyzing a least a portion of the $CS_2$ to form a purified alkyl sulfide product stream.

2. The process of claim 1, wherein the alkyl sulfide has the general formula $R^1$—S—$R^2$, wherein:
   $R^1$ is a $C_1$ to $C_{18}$ substituted or unsubstituted, cycloalkyl group or linear or branched alkyl group; and
   $R^2$ is a $C_1$ to $C_{18}$ substituted or unsubstituted, cycloalkyl group or linear or branched alkyl group.

3. The process of claim 1, wherein the alkyl sulfide comprises dimethyl sulfide (DMS).

4. The process of claim 1, wherein the mixed-metal catalyst comprises two or more Group 3-12 transition metals.

5. The process of claim 4, wherein the mixed-metal catalyst comprises two or more of cobalt (Co), molybdenum (Mo), and nickel (Ni).

6. The process of claim 1, wherein the mixed-metal catalyst comprises a cobalt-molybdenum (CoMo) catalyst comprising:
   from about 1 wt. % to about 5 wt. % cobalt, and
   from about 3 wt. % to about 20 wt. % molybdenum.

7. The process of claim 1, wherein the mixed-metal catalyst comprises a nickel-molybdenum (NiMo) catalyst comprising:
   from about 1 wt. % to about 5 wt. % nickel, and
   from about 3 wt. % to about 20 wt. % molybdenum.

8. The process of claim 1, wherein the mixed-metal catalyst further comprises a mixed-metal catalyst support comprising alumina, silica, magnesia, boria, titania, zirconia, a zeolite, or combinations thereof.

9. The process of claim 8, wherein the mixed-metal catalyst support comprises alumina.

10. The process of claim 1, where the mixed-metal catalyst comprises a CoMo catalyst supported on alumina.

11. The process of claim 1, wherein:
    the alkyl sulfide composition comprises at least 1000 ppm of $CS_2$; and
    the purified alkyl sulfide product stream comprises less than about 500 ppm of $CS_2$.

12. The process of claim 11, wherein the purified alkyl sulfide product stream comprises less than about 100 ppm of $CS_2$.

13. The process of claim 11, wherein the purified alkyl sulfide product stream comprises less than about 10 ppm of $CS_2$.

14. The process of claim 1, wherein:
    the temperature is in a range of from about 125° C. to about 225° C.;
    the pressure is in a range of about 10 psig to about 100 psig; and
    the WHSV is in a range of from about 0.20 to about 1.5.

15. The process of claim 4, wherein:
    the temperature is in a range of from about 130° C. to about 150° C.;
    the pressure is in a range of about 25 psig to about 75 psig; and
    the WHSV is in a range of from about 0.25 to about 0.75.

16. The process of claim 1, wherein the process is performed in one or more vessels selected from a flow reactor, a continuous reactor, a packed tube, a stirred tank reactor, and combinations thereof.

17. The process of claim 16, wherein the one or more vessels comprise at least two vessels arranged in series or in parallel.

18. The process of claim 1, wherein contacting the aqueous alkyl sulfide composition with the mixed-metal catalyst occurs over a time period in a range of about 1 minute to about 48 hours.

19. The process of claim 2, wherein contacting the aqueous alkyl sulfide composition with the mixed-metal catalyst occurs over a time period in a range of about 5 minutes to about 8 hours.

20. The process of claim 1, wherein the purified alkyl sulfide product stream comprises less than about 5 ppm of $CS_2$.

21. The process of claim 1, wherein the temperature is in a range of from about 125° C. to about 175° C.

22. The process of claim 1, wherein contacting the alkyl sulfide composition with the water is performed at a molar ratio of water to $CS_2$ in a range of from about 25:1 to about 100:1.

23. A process for purifying an alkyl sulfide composition, the process comprising:
(i) contacting the alkyl sulfide composition comprising carbon disulfide ($CS_2$) and at least 85 wt. % dimethyl sulfide (DMS) with water to form an aqueous alkyl sulfide composition;
(ii) contacting the aqueous alkyl sulfide composition with a mixed-metal catalyst at
   a temperature in a range of from about 100° C. to about 300° C.,
   a pressure in a range of from about 5 psig to about 300 psig,
   a molar ratio of water to $CS_2$ in a range of from about 10:1 to about 100:1, and
   a weight hourly space velocity (WHSV) in a range of from about 0.05 to about 5; and
(iii) hydrolyzing a least a portion of the $CS_2$ to form a purified alkyl sulfide product stream.

24. The process of claim 23, wherein contacting the alkyl sulfide composition with the water is performed at a molar ratio of water to $CS_2$ in a range of from about 25:1 to about 100:1.

25. The process of claim 23, wherein:
the alkyl sulfide composition comprises at least 1000 ppm of $CS_2$; and
the purified alkyl sulfide product stream comprises less than about 100 ppm of $CS_2$.

26. The process of claim 23, wherein the mixed-metal catalyst comprises two or more of cobalt (Co), molybdenum (Mo), and nickel (Ni).

27. The process of claim 23, where the mixed-metal catalyst comprises a CoMo catalyst supported on alumina.

28. The process of claim 23, wherein:
the temperature is in a range of from about 125° C. to about 225° C.;
the pressure is in a range of about 10 psig to about 100 psig; and
the WHSV is in a range of from about 0.20 to about 1.5.

29. The process of claim 23, wherein:
the temperature is in a range of from about 130° C. to about 150° C.;
the pressure is in a range of about 25 psig to about 75 psig; and
the WHSV is in a range of from about 0.25 to about 0.75.

30. The process of claim 23, wherein the process is performed in one or more vessels selected from a flow reactor, a continuous reactor, a packed tube, a stirred tank reactor, and combinations thereof.

31. The process of claim 23, wherein the alkyl sulfide composition comprises at least 90 wt. % dimethyl sulfide (DMS).

32. The process of claim 23, wherein the alkyl sulfide composition comprises at least 95 wt. % dimethyl sulfide (DMS).

* * * * *